United States Patent [19]

Nakano et al.

[11] Patent Number: 5,750,730
[45] Date of Patent: May 12, 1998

[54] FLUORINE-CONTAINING DIOXOLANE COMPOUND, ELECTROLYTIC SOLUTION COMPOSITION, BATTERY AND CAPACITOR

[75] Inventors: Tomoharu Nakano; Katsuji Shiono. both of Kyoto, Japan

[73] Assignee: Sanyo Chemical Industries, Ltd., Kyoto, Japan

[21] Appl. No.: 777,867

[22] Filed: Dec. 31, 1996

[30] Foreign Application Priority Data

| Jan. 10, 1996 | [JP] | Japan | 8-020452 |
| Jan. 10, 1996 | [JP] | Japan | 8-020453 |
| Feb. 19, 1996 | [JP] | Japan | 8-056720 |
| Feb. 19, 1996 | [JP] | Japan | 8-056721 |

[51] Int. Cl.$^6$ ............ C07D 317/16; C07D 317/38; C07D 317/42
[52] U.S. Cl. ............................ 549/229; 549/455
[58] Field of Search ............................ 549/229, 455

[56] References Cited

FOREIGN PATENT DOCUMENTS

| 62-290071 | 12/1987 | Japan . |
| 6-10995 | 2/1994 | Japan . |
| 7-240232 | 9/1995 | Japan . |
| 7-312227 | 11/1995 | Japan . |

OTHER PUBLICATIONS

Kuroboshi et al, Synlett, vol. 4, pp. 251–252, 1994.

Jehoshua et al, J. Chem. Soc., Perkins Trans., 2 (11), pp. 1729–1739, 1989.

*Primary Examiner*—Ba K. Trinh
*Attorney, Agent, or Firm*—Shinjyu Office of Patent Attorneys

[57] ABSTRACT

Fluorine-containing dioxolane compounds and electrolytic solution compositions containing the fluorine-containing dioxolane compounds are disclosed. Lithium secondary batteries or electric double layer capacitors, having various improved characteristics such as improved charge and discharge cycle life or improved durability over a long period of time can be obtained by using the electrolytic solution compositions.

6 Claims, 2 Drawing Sheets

FLUORINE-CONTAINING DIOXOLANE COMPOUND, ELECTROLYTIC SOLUTION COMPOSITION, BATTERY AND CAPACITOR

BACKGROUND OF THE INVENTION

A. Field Of The Invention

The present invention relates to novel fluorine-containing dioxolane compounds which are suitable for use as media in a secondary battery, such as a lithium secondary battery, or in a capacitor, such as an electric double layer capacitor. More precisely, these compounds are suitable for use as organic solvents for an electrolytic solution in the above-described secondary battery or capacitor.

B. Description Of The Prior Art

In recent years, there has been a remarkable amount of development in the large scale integration (LSI) of electronic devices, which has led to a tremendous reduction in the size and weight of these devices. This has led to an increase in the performance required of the electrolytic solutions used in the secondary batteries and capacitors incorporated into these devices.

For example, increasing expectations have been placed on lithium batteries as a battery which can supply high energy densities and having excellent storage properties. A miniaturized and lightweight lithium battery is already in use as a primary battery, but because it is a primary battery its field of use is limited.

On the other hand, secondary batteries in which metallic lithium is used as a negative electrode have shown great promise. However, these types of batteries often do not have a sufficient charge and discharge cycle life, due to the precipitation of dendrite-form lithium.

Thus, there has been a great deal of research in the field of carbon materials which can litiate and delitiate, as well as organic solvents which can serve as an electrolytic solution suitable for the carbon material. Examples of such organic solvents include mixtures of propylene carbonate or ethylene carbonate with diethyl carbonate.

In addition, the rapid increase in demand for semiconductor memory chips has also increased interest in the use of electric double layer capacitors as an electric source for memory back-up during sudden power failures. Capacitors which can instantaneously charge and discharge a farad order of electric capacity by utilizing electric energy accumulated in an electric double layer formed at the interface between activated carbon and an electrolytic solution are especially desirable. In addition, because a large amount of electricity can be discharged instantaneously, these types of electric double layer capacitors are increasingly expected to be a source of electric power for electric vehicles.

These types of electric double layer capacitors have conventionally used aqueous electrolytic solutions such as sulfuric acid or potassium hydroxide, or organic electrolytic solutions prepared by dissolving an electrolyte such as tetraalkylammonium salts into an organic solvent such as propylene carbonate, butylene carbonate, γ-butyrolactone, acetonitrile or dimethyl formamide.

However, when these types of conventional organic solvents are used in lithium secondary batteries, a sufficient charge and discharge cycle life cannot be obtained due to decomposition reactions, which are due to oxidation and reduction during charging and discharging.

In addition, when these types of conventional organic solvents are used in electric double layer capacitors, the withstand voltage per unit cell is only 2.5 V, and this is insufficient for the purposes of memory back-up or as an electric power source for electric vehicles.

Miniaturization of the capacitor can be realized if the withstand voltage is increased to 3.0 V or more. However, if a voltage of 2.5 V or more is applied to the conventional electric double layer capacitor, a polymerization reaction or gas generation will occur due to the electrolysis of the electrolytic solution, and in particular the decomposition of the solvent. As a result, various disadvantages occur such as liquid leakage, the expansion of the exterior case, an increase in direct current resistance, or a decrease in capacity.

Thus, in order to maximize the effectiveness of lithium secondary batteries and electric double layer capacitors which use organic electrolytic solutions, a organic solvent having a wider redox potential is needed. More specifically, an organic solvent is needed which has an oxidation potential closer to the noble side and a reduction potential closer to the base side.

SUMMARY OF THE INVENTION

It is therefore a first object of the present invention to obtain an organic solvent having a wider redox potential, with an oxidation potential closer to the noble side and a reduction potential closer to the base side.

A second object of the present invention is to obtain an electrolytic solution composition for use in a secondary battery or a capacitor in which the organic solvent has a wider redox potential.

A third object of the present invention is to obtain a lithium secondary battery having an improved charge and discharge cycle life.

A fourth object of the present invention is to obtain an electric double layer capacitor in which a high voltage can be applied over a long period of time.

As a result of an extensive effort to attain the above-described objects, the present inventors have found specific fluorine-containing dioxolane compounds suitable as the organic solvent. The present invention has been completed based on this finding.

Thus, the present invention provides a fluorine-containing dioxolane compound (a1) represented by the following formula (1):

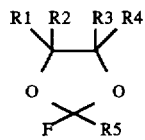

in which R1, R2, R3 and R4 each represents a hydrogen atom or an alkyl group having 1 to 4 carbon atoms, and R5 represents a hydrogen atom, fluorine atom or a —CFXY group in which X and Y each represents a hydrogen atom, a fluorine atom or an alkyl group having 1 to 4 carbon atoms.

The present invention also provides a fluorine-containing dioxolane compound (a2) represented by the following formula (2):

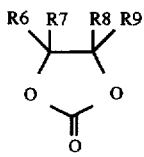

in which at least one of R6, R7, R8 and R9 represents an —CHF—X group in which X represents a hydrogen atom, a fluorine atom or an alkyl group having 1 to 4 carbon atoms, and the remaining R groups each represents a hydrogen atom or an alkyl group having 1 to 4 carbon atoms.

The present invention also provides an electrolytic solution composition (E-1) in which an electrolyte is dissolved in an organic solvent (s1) comprising the compound (a1).

The present invention also provides an electrolytic solution composition (E-2) in which an electrolyte is dissolved in an organic solvent (s2) comprising the compound (a2).

The present invention also provides a lithium secondary battery which includes therein the electrolytic solution composition (E-1).

The present invention also provides a lithium secondary battery which includes therein the electrolytic solution composition (E-2).

The present invention also provides an electric double layer capacitor which includes therein the electrolytic solution composition (E-1).

The present invention also provides an electric double layer capacitor which includes therein the electrolytic solution composition (E-2).

Other objects, features, aspects and advantages of the present invention will be apparent from the following detailed description of the present invention when taken in conjunction with the accompanying drawings.

DESCRIPTION OF THE PREFERRED EMBODIMENTS

Figure 1:
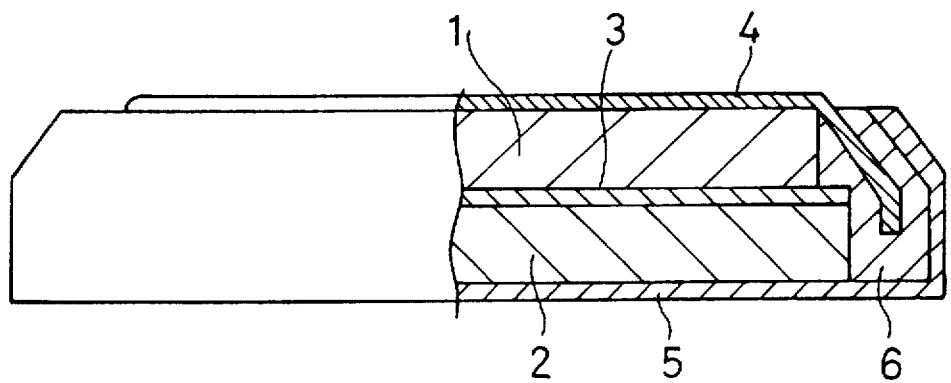
FIG. 1 shows a part cross sectional view of a lithium secondary battery according to one embodiment of the present invention.

The present invention provides a fluorine-containing dioxolane compound (a1) represented by the following formula (1):

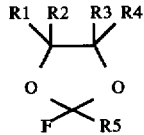

in which R1, R2, R3 and R4 each represents a hydrogen atom or an alkyl group having 1 to 4 carbon atoms, and R5 represents a hydrogen atom, fluorine atom or a —CFXY group in which X and Y each represents a hydrogen atom, a fluorine atom or an alkyl group having 1 to 4 carbon atoms.

Specific examples of alkyl groups having 1 to 4 carbon atoms for R1, R2, R3 and R4 , or the alkyl group having 1 to 4 carbon atoms for X and Y in the —CFXY group, include methyl, ethyl, n- or -i propyl, and n-, -i or t-butyl groups.

Specific examples of the fluorine-containing dioxolane compound (a1) used in the present invention include 2-fluoro -1,3-dioxolane, 2-fluoro-4-methyl-1,3-dioxolane, 2,2-difluoro -1,3-dioxolane, 2,2-difluoro-4-methyl-1,3-dioxolane, 2,2-difluoro-4,5-dimethyl-1,3-dioxolane, 2,2-difluoro -4-ethyl-1,3-dioxolane, 2,2-difluoro-4-n-propyl-1, 3-dioxolane, 2-fluoro-2-(1-fluoroethyl)-1,3-dioxolane, 2-fluoro -2-(1-fluoro-n-propyl)-1,3-dioxolane, 2-fluoro-2-fluoromethyl-1,3-dioxolane, 2-fluoro-2-difluoromethyl-1,3-dioxolane, and 2-fluoro-2-trifluoromethyl-1,3-dioxolane.

In the fluorine-containing dioxolane compound (a1), a compound in which R5 is a fluorine atom can be obtained by reacting a cyclic thioncarbonate with a fluorination agent in the presence of an oxidizing agent. The cyclic thioncarbonate is represented by the following formula (3):

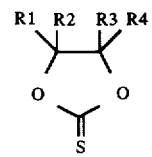

in which R1, R2, R3 and R4 each represents hydrogen atom or an alkyl group having 1 to 4 carbon atoms.

Examples of the oxidizing agent used include N-haloimides such as N-iodosuccinimide (NIS), N-bromosuccinimide (NBS) or N-chlorosuccinimide (NCS), 1,3-dibromo -5,5-dimethylhydantoin (DBH), methyl fluorosulfate, and lead acetate. Of those, N-haloimides are preferred from the standpoint of ease of handling.

Examples of the fluorination agent used include potassium fluoride (KF)/phase-transfer catalyst, KF/inorganic carrier, spray dry KF, tetraalkylammonium fluoride, and tetraalkylammonium fluoride-(hydrogen fluoride) complex. Of those, tetraalkylammonium fluoride-(hydrogen fluoride) complex having low moisture absorption and high nucleophilic properties is preferred.

The reaction solvent which can be used are organic solvents such as dichloromethane, 1,2-dichloroethane, chloroform, benzene or toluene.

As for reaction temperature, the oxidizing agent should be added at about −5° to 0° C., and then the temperature of the mixture should be gradually raised up to near room temperature.

The reaction time is not particularly limited, however the end of the reaction can be defined as the moment in which the cyclic thioncarbonate has been completely consumed.

After completion of the reaction, the fluorine-containing dioxolane (a1) can be isolated from the reaction mixture by general separation means such as filtration, extraction or washing. Further, if necessary, the compound thus obtained can be purified with recrystallization, distillation, column chromatography or the like.

The present invention also provides a fluorine-containing dioxolane compound (a2) represented by the following formula (2):

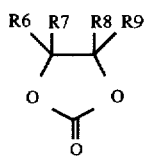

in which at least one of R6, R7, R8 and R9 represents an —CHF—X group in which X represents a hydrogen atom, a fluorine atom or an alkyl group having 1 to 4 carbon atoms, and the remaining R groups each represents a hydrogen atom or an alkyl group having 1 to 4 carbon atoms.

The fluorine-containing dioxolane compound (a2) can also be referred to as a fluorine-containing cyclic carbonate compound.

Specific examples of the alkyl group having 1 to 4 carbon atoms for R6, R7, R8 and R9 , or the alkyl group having 1 to 4 carbon atoms for X in —CHF—X, include methyl, ethyl, n- or iso-propyl, and n-, iso- or t-butyl groups. At least one of R6, R7, R8 and R9 is a —CHF—X group, but considering the molecular weight, it is preferred that only one R group is the —CHF—X group.

Specific examples of (a2) used in the present invention include 4-monofluoromethyl-1,3-dioxolan-2-one, 4-difluoromethyl -1,3-dioxolan-2-one, 4-monofluoromethyl-5-methyl -1,3-dioxolan-2-one, 4-monofluoromethyl-4-methyl-1,3-dioxolan-2-one, 4-monofluoromethyl-5,5-dimethyl-1,3-dioxolan-2-one, 4-(1-fluoroethyl)-1,3-dioxolan-2-one, 4-(1fluoro-n-propyl) -1,3-dioxolan-2-one, and 4-(1-fluoro-n-butyl) -1,3-dioxolan-2-one.

A method of producing the fluorine-containing dioxolane compound (a2) is as follows. For example, the fluorine-containing dioxolane compound (a2) can be obtained by reacting a diol with dimethyl carbonate in the presence of a catalyst such as KOH. The diol is represented by the following formula (4):

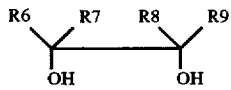

wherein at least one of R6, R7, R8 and R9 is a —CHF—X group, in which X represents a hydrogen atom, a fluorine atom or an alkyl group having 1 to 4 carbon atoms, and the remaining R groups each represents a hydrogen atom or an alkyl group having 1 to 4 carbon atoms.

The fluorine-containing dioxolanes (a1) and (a2) of the present invention are useful as organic solvents for various electrolytic solutions. Further, (a1) and (a2) can be used together in optional proportions as an organic solvent for electrolytic solutions. Hereinafter, (a1), (a2) and the combined use thereof will be referred to as a fluorine-containing dioxolane (a) for simplicity.

If necessary, at least one type of a compound (b) selected from the group consisting of cyclic or chain carbonates (b1), chain carboxylic acid esters (b2), cyclic or chain ethers (b3), lactone compounds (b4), nitrile compounds (b5) and amide compounds (b6) can be used as a co-solvent with the fluorine-containing dioxolane (a) as the organic solvent for the electrolytic solution.

Examples of (b1) include ethylene carbonate, propylene carbonate, dimethyl carbonate, methyl ethyl carbonate and diethyl carbonate.

Examples of (b2) include methyl acetate and methyl propionate.

Examples of (b3) include tetrahydrofuran, 1,3-dioxolane and 1,2-dimethoxyethane.

An example of (b4) includes γ-butyrolactone.

An example of (b5) includes acetonitrile.

An example of (b6) includes dimethylformamide.

In using (b), care should be taken because the preferred compound varies according to the purpose for which the electrolytic solution is to be used. For example, when the electrolytic solution is to be used in a lithium secondary battery, (b1) and (b2) are preferred, but when the electrolytic solution is to be used in a electric double layer capacitor, (b1), (b3), (b4), (b5) and (b6) are preferred.

The mixing ratio of compound (b) to the fluorine-containing dioxolane (a) is generally b/a=(0.1-2)/1, preferably b/a=(0.5-1.5)/1, and more preferably b/a=(0.5-1)/1, by weight.

In preparing the organic electrolytic solution using the above-mentioned solvents, there is no particular restrictions on the electrolyte to be used.

In the case of lithium secondary batteries, $LiBF_4$, $LiPF_6$, $LiAsF_6$, $LiClO_4$, $LiCF_3SO_3$, $LiN(CF_3SO_2)_2$ and the like can be used, whereas in the case of electric double layer capacitors, tetraalkylammonium tetrafluoroborate, hexafluorophosphate, perchlorate, hexafluoroarsenate, trifluoromethanesulfonate and the like can be used.

The present invention is explained in more detail by reference to the following examples, but it should be understood that the invention is not construed as being limited thereto.

SYNTHESIS OF FLUORINE-CONTAINING DIOXOLANE

SYNTHESIS EXAMPLE 1

Production of 2,2-difluoro-4-methyl-1,3-dioxolane 47.2 g (0.40 mol) of propylene thionocarbonate was dissolved in 600 ml of dichloromethane and 301.0 g (1.00 mol) of tetra-n-butyl-N-ammonium dihydrogen trifluoride $(n-C_4H_9)_4NF(HF)_2$, and the resulting mixture was cooled to 0° C.

180.0 g (0.80 mol) of N-iodosuccinimide was added to the above mixture at 0° C. or less, and the resulting mixture was stirred at room temperature for 2 hours.

After performing extraction with ether and distilling off the ether, the liquid thus obtained was distilled under reduced pressure to obtain 37.2 g of 2,2-difluoro-4-methyl-1,3-dioxolane (yield 75.0%). An $^1$H-NMR spectrum was obtained, and the following data was observed (ppm): 1.37 (d,3H) 4.06 (t,1H) 4.57 (t, 1H) 4.83–4.96 (m, 1H). An elemental analysis was performed, and the following values were observed:

|   | Theoretical value (%) | Actual value (%) |
|---|---|---|
| C | 38.72 | 38.80 |
| H | 4.87 | 4.77 |
| F | 30.62 | 30.51 |
| O | 25.79 | 25.92 |

SYNTHESIS EXAMPLE 2

Production of 2,2-difluoro-1,3-dioxolane:

41.6 g (0.40 mol) of ethylene thionocarbonate was dissolved in 600 ml of dichloromethane and 301.0 g (1.00 mol)

of tetra-n-butyl-N-ammonium dihydrogen trifluoride $(n-C_4H_9)_4NF(HF)_2$, and the resulting mixture was cooled to 0° C.

180.0 g (0.80 mol) of N-iodosuccinimide was added to the above mixture at 0° C. or less, and the resulting mixture was stirred at room temperature for 2 hours.

After performing extraction with ether and distilling off the ether, the liquid thus obtained was distilled under reduced pressure to obtain 30.9 g of 2,2-difluoro-1,3-dioxolane (yield 70.2%). An $^1$H-NMR spectrum was obtained and the following data was observed (ppm): 4.17 (t,4H). An elemental analysis was performed and the following values were observed:

|   | Theoretical value (%) | Actual value (%) |
|---|---|---|
| C | 32.74 | 32.80 |
| H | 3.67 | 3.63 |
| F | 34.52 | 34.41 |
| O | 29.07 | 29.16 |

Both 2,2-difluoro-4-methyl-1,3-dioxolane and 2,2-difluro-1,3-dioxolane obtained in Synthesis Examples 1 and 2 above, and propylene carbonate and, 2 trifluoromethyl-1,3-dioxolane as a comparison, were evaluated for their electrochemical stability.

SYNTHESIS EXAMPLE 3

Production of 4-monofluoromethyl-1,3-dioxolan-2-one 2.0 g of potassium hydroxide and 500 g of dimethyl carbonate were added to 110.0 g (1.17 mol) of 3-fluoro-1,2-propanediol, and the resulting mixture was stirred at 60° C. for 8 hours. After filtering off potassium hydroxide, the mixture was distilled to obtain 98.0 g of 4-monofluoromethyl-1,3-dioxolan-2-one (yield 70.0%). An $^1$H-NMR spectrum was obtained and the following data was observed (ppm): 4.28–4.35 (m,1H) 4.55–4.62 (m,2H) 4.71–4.78 (m,1H) 4.97–5.13 (m,1H). An elemental analysis was performed, and the following values were observed:

|   | Theoretical value (%) | Actual value (%) |
|---|---|---|
| C | 40.01 | 40.10 |
| H | 4.20 | 4.22 |
| F | 15.82 | 15.75 |
| O | 39.97 | 39.93 |

SYNTHESIS EXAMPLE 4

Production of 4-(1-fluoroethyl)-1,3-dioxolan-2-one 2.0 g of potassium hydroxide and 50 g of dimethyl carbonate were added to 108.0 g (1.00 mol) of 3-fluoro-1,2-butanediol, and the resulting mixture was stirred at 60° C. for 12 hours. After filtering off potassium hydroxide, the mixture was distilled to obtain 101.2 g of 4-(1-fluoroethyl)-1,3-dioxolan-2-one (yield 75.5%). An elemental analysis was performed and the following values were observed:

|   | Theoretical value (%) | Actual value (%) |
|---|---|---|
| C | 44.78 | 44.70 |
| H | 5.26 | 5.22 |
| F | 14.17 | 14.33 |
| O | 35.79 | 35.75 |

PRODUCTION OF ELECTROLYTIC SOLUTION COMPOSITION

EXAMPLES 1 TO 4

A composition obtained by dissolving $LiPF_6$ in 2,2-difluoro-4-methyl-1,3-dioxolane in the proportion of 0.65 mol/L (Example 1), a composition obtained by dissolving $(C_2H_5)_4NBF_4$ in 2,2-difluoro-4-methyl-1,3-dioxolane in the proportion of 0.65 mol/L (Example 2), a composition obtained by dissolving $(C_2H_5)_3NCH_3 \cdot BF_4$ in 2,2-difluoro-4-methyl -1,3-dioxolane in the proportion of 0.65 mol/L (Example 3), and a composition obtained by dissolving N-methyl-N-ethyl pyrrolidinium tetrafluoroborate in 2,2-difluoro -4-methyl-1,3-dioxolane in the proportion of 0.65 mol/L (Example 4) were prepared.

EXAMPLES 5 AND 6

A composition obtained by dissolving $LiPF_6$ in 2,2-difluoro -1,3-dioxolane in the proportion of 0.65 mol/L (Example 5), and a composition obtained by dissolving $(C_2H_5)_4NBF_4$ in 2,2-difluoro-1,3-dioxolane in the proportion of 0.65 mol/L (Example 6) were prepared.

EXAMPLES 7 TO 10

A composition obtained by dissolving $LiPF_6$ in 4-monofluoromethyl -1,3-dioxolan-2-one in the proportion of 0.65 mol/L (Example 7), a composition obtained by dissolving $(C_2H_5)_4NBF_4$ in 4-monofluoromethyl -1,3-dioxolan-2-one in the proportion of 0.65 mol/L (Example 8), a composition obtained by dissolving $(C_2H_5)_3NCH_3 \cdot BF_4$ in 4-monofluoromethyl -1,3-dioxolan-2-one in the proportion of 0.65 Mol/L (Example 9), and a composition obtained by dissolving N-methyl-N-ethyl pyrrolidinium tetrafluoroborate in 4-monofluoromethyl-1,3-dioxolan-2-one in the proportion of 0.65 mol/L (Example 10) were prepared.

EXAMPLES 11 AND 12

A composition obtained by dissolving $LiPF_6$ in 4-(1-fluoroethyl) -1,3-dioxolan-2-one in the proportion of 0.65 mol/L (Example 11), and a composition obtained by dissolving $(C_2H_5)_4NBF_4$ in 4-(1-fluoroethyl)-1,3-dioxolan-2-one in the proportion of 0.65 mol/L (Example 12) were prepared.

COMPARATIVE EXAMPLES 1 To 6

A composition obtained by dissolving $LiPF_6$ in propylene carbonate in the proportion of 0.65 mol/L (Comparative Example 1), a composition obtained by dissolving $(C_2H_5)_4NBF_4$ in propylene carbonate in the proportion of 0.65 mol/L (Comparative Example 2), a composition obtained by dissolving $LiPF_6$ in 2-trifluoromethyl-1,3-dioxolane in the proportion of 0.65 mol/L (Comparative Example 3), a composition obtained by dissolving $(C_2H_5)_4NBF_4$ in 2trifluoromethyl -1,3-dioxolane in the proportion of 0.65 mol/L (Comparative Example 4), a composition obtained by dissolving $LiPF_6$ in 4-trifluoromethyl-1,3-dioxolan-2-one in the proportion of 0.65 mol/L (Example 5), and a composition obtained by dissolving $(C_2H_5)_4NBF_4$ in 4-trifluoromethyl-1,3-dioxolan-2-one in the proportion of 0.65 mol/L (Example 6) were prepared as comparative examples.

EVALUATION EXAMPLE 1

Evaluation of redox potential width

The evaluation was conducted by the measurement of a potential scanning method using a three electrode cell. Platinum was used for a working electrode and a counter electrode, and silver-silver chloride was used for a reference electrode. Scan rate was conducted at 100 mV/sec, and potentials, in which rise of electric current was observed at the oxidation side and the reduction side, were defined as an oxidation potential and a reduction potential, respectively. The results converted into SCE standard are shown in Table 1.

TABLE 1

| | Organic solvent | Electrolyte | Oxidation potential (V vs SCE) | Reduction potential (V vs SCE) |
|---|---|---|---|---|
| Example 1 | 2,2-Difluoro-4-methyl-1,3-dioxolane | $LiPF_6$ | 3.5 | −4.0 |
| Example 2 | | $(C_2H_5)_4NBF_4$ | 3.6 | −4.2 |
| Example 3 | | $(C_2H_5)_3NCH_3BF_4$ | 3.6 | −4.2 |
| Example 4 | | N-Methyl-N-ethyl pyrrolidinium tetrafluoro borate | 3.6 | −4.1 |
| Example 5 | 2,2-Difluoro-1,3-dioxolane | $LiPF_6$ | 3.8 | −3.7 |
| Example 6 | | $(C_2H_5)_4NBF_4$ | 3.7 | −3.7 |
| Example 7 | 4-Monofluoro methyl-1,3-dioxolan-2-one | $LiPF_6$ | 3.3 | −3.3 |
| Example 8 | | $(C_2H_5)_4NBF_4$ | 3.6 | −3.3 |
| Example 9 | | $(C_2H_5)_3NCH_3BF_4$ | 3.6 | −3.3 |
| Example 10 | | N-methyl-N-ethyl pyrrolidinium tetrafluoro borate | 3.5 | −3.0 |
| Example 11 | 4-(1-Fluoroethyl)-1,3-dioxolan-2-one | $LiPF_6$ | 3.3 | −3.2 |
| Example 12 | | $(C_2H_5)_4NBF_4$ | 3.5 | −3.3 |
| Comparative Example 1 | Propylene carbonate | $LiPF_6$ | 3.0 | −3.0 |
| Comparative Example 2 | | $(C_2H_5)_4NBF_4$ | 3.1 | −3.1 |
| Comparative Example 3 | 2-Trifluoro methyl-1,3-dioxolan-2 | $LiPF_6$ | 2.7 | −2.0 |
| Comparative Example 4 | | $(C_2H_5)_4NBF_4$ | 2.6 | −2.0 |
| Comparative Example 5 | 4-Trifluoro methyl-1,3-dioxolan-2-one | $LiPF_6$ | 2.7 | −2.0 |
| Comparative Example 6 | | $(C_2H_5)_4NBF_4$ | 2.5 | −2.2 |

It can be seen from the results shown in Table 1 above that the fluorine-containing dioxolane used in Examples 1 to 12 are such that the oxidation potential is expanded to closer to the noble side and the reduction potential is expanded closer to the base side, thus providing a wide redox potential width, as compared with the propylene carbonate used in Comparative Examples 1 and 2.

2-Trifluoromethyl-1,3-dioxolane, having no fluorine atom at the 2-position used in Comparative Examples 3 and 4, and 4-trifluoromethyl-1,3-dioxolan-2-one, having $CF_3$ at the 4-position used in Comparative Examples 5 and 6, are such that the oxidation potential shifts to the base side and the reduction potential shifts to the noble side, making the redox potential width narrow, which is undesirable.

EVALUATION EXAMPLE 2

Evaluation of electroconductivity vs temperature

The electroconductivity of the organic electrolytic solution used in Examples 1 and 5 and Comparative Example 1 was measured at each temperature.

The results obtained are shown in Table 2 below.

TABLE 2

| | Electroconductivity (ms/cm) | | |
|---|---|---|---|
| | −10° C. | 0° C. | 25° C. |
| Example 1 | 1.6 | 2.6 | 6.1 |
| Example 5 | 1.5 | 2.6 | 6.0 |
| Comparative Example 1 | 1.2 | 2.1 | 5.1 |

It can be seen from the results shown in Table 2 above that the fluorine-containing dioxolane used in Examples 1 and 5 has excellent electroconductivity as compared with propylene carbonate used in Comparative Example 1.

PRODUCTION EXAMPLE OF LITHIUM SECONDARY BATTERY

EXAMPLE 13

FIG. 1 is a part cross sectional view of a lithium secondary battery prepared according to the present examples. In FIG. 1, 1 is graphite, 2 is a cathode material, 3 is a porous separator, 4 is an anode container, 5 is a cathode container, and 6 is a gasket.

The secondary battery shown in FIG. 1 was prepared according to the following procedures.

$LiCoO_2$ was mixed with acetylene black as a conducting agent and polyethylene powder as a binder. The resulting mixture was pressure molded to prepare a cathode material 2. This material 2 was adhered by contact bonding on a net formed of nickel placed on the bottom of a cathode container 5 formed of stainless steel.

Next, a porous separator 3 formed of polypropylene was placed on the above material. An organic electrolytic solution prepared by dissolving $LiPF_6$ in a mixed solvent of 2,2-difluoro-4-methyl-1,3-dioxolane and diethyl carbonate in equivalent volume at a concentration of 1.0 mol/L was poured into the container, and a gasket 6 was then inserted therein.

A anode container 4 formed of stainless steel and having graphite 1 adhered thereto was placed on the separator 3. The opening edge portion of the cathode container 5 was bent inwardly and the closed portion was sealed with a hermetic seal, thus creating a lithium secondary battery in which an organic electrolytic solution was impregnated in the cathode material 2, graphite 1 and the separator 3, as shown in FIG. 1.

EXAMPLE 14

A lithium secondary battery having the same structure as shown in FIG. 1 was prepared in the same manner as in Example 13 except for using an organic electrolytic solution prepared by dissolving $LiPF_6$ in a mixed solvent of 2,2-difluoro-1,3-dioxolane and diethyl carbonate in equivalent volume at a concentration of 1.0 mol/L.

EXAMPLE 15

A lithium secondary battery having the same structure as shown in FIG. 1 was prepared in the same manner as in Example 13 except for using an organic electrolytic solution prepared by dissolving $LiPF_6$ in a mixed solvent of 4-monofluoromethyl-1,3-dioxolan-2-one and diethyl carbonate in equivalent volume at a concentration of 1.0 mol/L.

EXAMPLE 16

A lithium secondary battery having the same structure as shown in FIG. 1 was prepared in the same manner as in Example 13 except for using an organic electrolytic solution prepared by dissolving $LiPF_6$ in a mixed solvent of 4-(1-fluoroethyl)-1,3-dioxolan-2-one and diethyl carbonate in equivalent volume at a concentration of 1.0 mol/L.

COMPARATIVE EXAMPLE 7

As a comparative example, a lithium secondary battery having the same structure as shown in FIG. 1 was prepared in the same manner as in Example 13 except for using an electrolytic solution composition prepared by dissolving $LiPF_6$ in a mixed solvent of propylene carbonate and diethyl carbonate in equivalent volume at a concentration of 1.0 mol/L, in place of the above-described organic electrolytic solution composition.

EVALUATION EXAMPLE 3

Cycle life of the lithium secondary battery

Cycle life were compared between the lithium secondary batteries obtained in Examples 13 to 16 above and the lithium secondary battery obtained in Comparative Example 7 above as follows.

Figure 2:
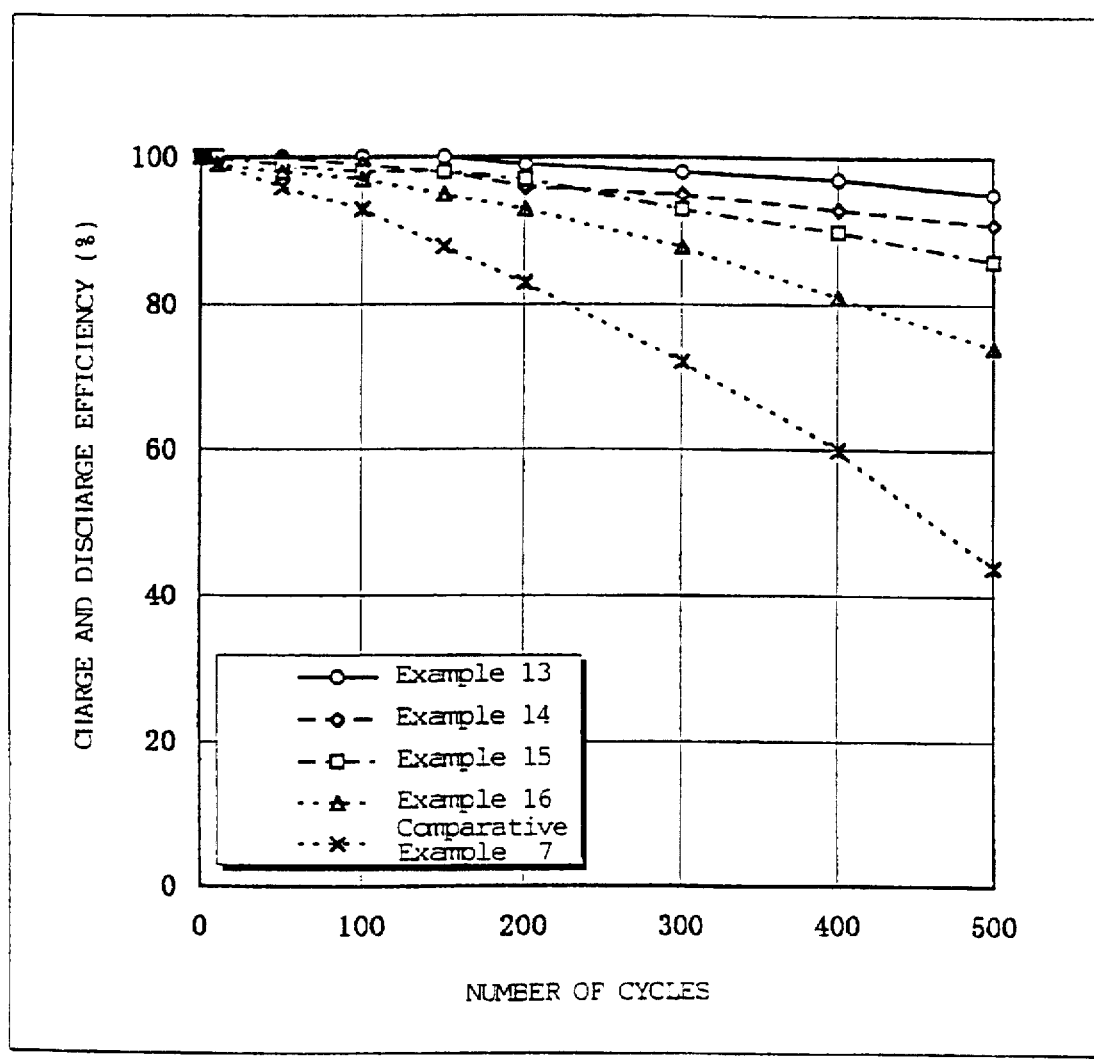
FIG. 2 is a graph showing a comparison of the charge and discharge cycle life of batteries using various organic solvents.

The upper limit voltage was set to 4.2 V, and each battery was charged at 1 mA for 10 hours under constant current. The battery was then discharged to the end voltage of 3.0 V at a constant current of 1 mA. This procedure was counted as one cycle of charge and discharge, and was repeated for a predetermined number of cycles. FIG. 2 is a graph plotting the charge and discharge efficiency as a function of the number of cycles.

As shown in FIG. 2, it is apparent that Examples 13 to 16 show good charge and discharge characteristics as compared with Comparative Example 7.

PRODUCTION EXAMPLE OF ELECTRIC DOUBLE LAYER CAPACITOR

EXAMPLE 17

Figure 3:
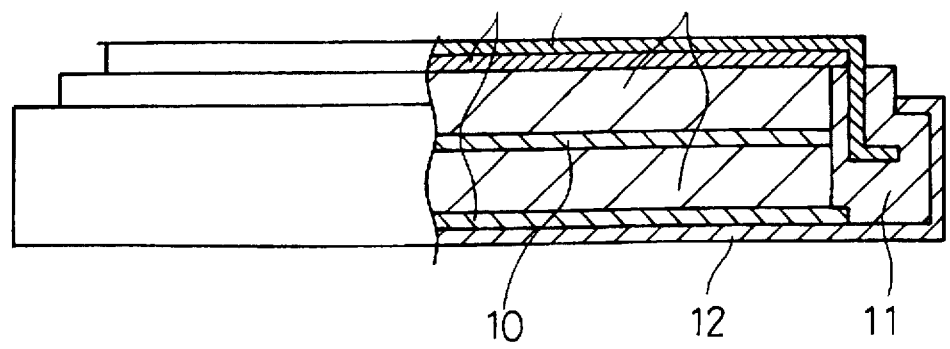
FIG. 3 shows a part cross sectional view of an electric double layer capacitor according to one embodiment of the present invention.

FIG. 3 is a part cross sectional view showing the structure of the electric double layer capacitor prepared in the present examples. In FIG. 3, 7 is a cover, 8 is an aluminum current collector, 9 is a polarizable electrode, 10 is a separator, 11 is a gasket, and 12 is a casing.

The electric double layer capacitor shown in FIG. 3 was prepared according to the following procedures.

An active carbon fiber (specific surface area 2,500 $m^2/g$) was used as a material for the polarizable electrode 9. Then the aluminum current collector was formed on the fiber with a plasma spraying.

This assembly was welded to the casing 12 and the cover 7, and an electrolytic solution prepared by dissolving 0.65 mol/L of $(C_2H_5)_4NBF_4$ in 2,2-difluoro-4-methyl-1,3-dioxolane was impregnated therein.

Next, the separator 10 composed of a polypropylene porous membrane was superposed on the electrode 9 at the negative electrode side, the positive electrode side case 12 was superposed thereon, the gasket 11 was covered on the periphery of the negative electrode side case 7, and the periphery of the positive electrode side case 12 was calked with pressing to seal, thereby preparing a coin-type electric double layer capacitor in which the electrolytic solution was impregnated in the polarized electrode 9 and the separator 10.

EXAMPLE 18

An electric double layer capacitor having the same structure as shown in FIG. 3 was prepared in the same manner as in Example 17 except for using an organic electrolytic solution prepared by dissolving $(C_2H_5)_4NBF_4$ in 2,2-difluoro-1,3-dioxolane at a concentration of 0.65 mol/L.

EXAMPLE 19

An electric double layer capacitor having the same structure as shown in FIG. 3 was prepared in the same manner as in Example 17 except for using an organic electrolytic solution prepared by dissolving $(C_2H_5)_4NBF_4$ in 4-monofluoromethyl-1,3-dioxolan-2-one at a concentration of 0.65 mol/L.

EXAMPLE 20

An electric double layer capacitor having the same structure as shown in FIG. 3 was prepared in the same manner as in Example 17 except for using an organic electrolytic solution prepared by dissolving $(C_2H_5)_4NBF_4$ in 4-(1-fluoroethyl)-1,3-dioxolan-2-one at a concentration of 0.65 mol/L.

COMPARATIVE EXAMPLE 8

As a reference comparative example, an electric double layer capacitor having the same structure as shown in FIG. 3 was prepared in the same manner as in Example 17 above except for using an electrolytic solution composition prepared by dissolving $(C_2H_5)_4NBF_4$ in propylene carbonate at a concentration of 0.65 mol/L, in place of the above-described organic electrolytic solution.

EVALUATION EXAMPLE 4

Evaluation of the initial characteristics of an electric double layer capacitor

Electric capacity and internal resistance were measured as the initial characteristics of the electric double layer capacitors prepared above, as follows.

The capacitors were allowed to stand at 70° C. for 1,000 hours while applying a voltage of 3.3 V, and the electric capacity and the internal resistance of the capacitors after the passage of 1,000 hours were measured.

The electric capacity was measured from a discharge curve when the capacitor charged at 3.3 V was discharged at a constant electric current. Further, the internal resistance was measured with an LCR meter (frequency 1KHz).

The results obtained are shown in Table 3 below.

TABLE 3

| | Characteristic of Electric Double Layer Capacitor | | | | | |
|---|---|---|---|---|---|---|
| | Initial | | 3.3 V applied, 70° C. × 1,000 hours | | | |
| | Capacity (F) | Internal resistance (Ω) | Capacity (F) | Change (%) | Internal resistance (Ω) | Change (%) |
| Example 17 | 2.23 | 5.85 | 2.01 | −10 | 6.98 | 19 |
| Example 18 | 2.20 | 5.96 | 1.93 | −12 | 7.27 | 22 |
| Example 19 | 2.30 | 6.10 | 1.73 | −25 | 8.11 | 33 |
| Example 20 | 2.22 | 6.35 | 1.53 | −31 | 8.89 | 40 |
| Comparative Example 8 | 2.15 | 6.50 | 0 | −100 | x | x |

It can be seen from the results shown in Table 3 above that the capacitors obtained in Examples 17 to 20 show little change in capacity and internal resistance even after applying 3.3 V, which is higher than the conventional voltage, at 70° C. and maintaining that for 1,000 hours, as compared with the capacitor obtained in Comparative Example 8.

As described above, the organic solvent for electrolytic solution, comprising the fluorine-containing dioxolane according to the present invention, has an excellent redox potential width, and therefore is suitable for use in an organic solvent for electrolytic solution used in secondary batteries such as a lithium secondary battery, or in capacitors such as an electric double layer capacitor.

Further, when the organic solvent according to the present invention is used as, for example, an organic solvent in a lithium secondary battery, the cycle life of the battery can be markedly increased. Furthermore, when it is used as an organic solvent for an electric double layer capacitor, it can be used over a long period of time under high voltages, and this provides a large industrial value.

What is claimed is:

1. A fluorine-containing dioxolane compound (a1), said compound improving the electroconductivity of an electrolyte solution and represented by the following formula (1):

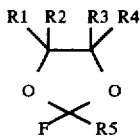

wherein R1, R2, R3 and R4 each represent a hydrogen atom or an alkyl group having 1 to 4 carbon atoms, and R5 represents a hydrogen atom, a fluorine atom or a —CFXY group wherein X and Y each represents a hydrogen atom, a fluorine atom or an alkyl group having 1 to 4 carbon atoms.

2. An electrolyte solution composition, which comprises an electrolyte dissolved in an organic solvent (s1) comprising said compound (a1) according to claim 1.

3. An electrolyte solution composition according to claim 2, wherein said organic solvent (s1) further comprises a co-solvent (a3) selected from the group consisting of cyclic or chain carbonates, chain carboxylic acid esters, cyclic or chain ethers, lactone compounds, nitrile compounds and amide compounds, in a weight ratio of a3/a1=(0.1 to 2)/1.

4. A fluorine-containing dioxolane compound (a2) represented by the following formula (2):

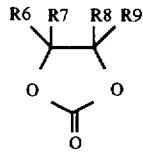

wherein at least one of R6, R7, R8 and R9 represents a —CHF—X group wherein X represents an alkyl group having 1 to 4 carbon atoms, and the remaining R groups each represents a hydrogen atom or an alkyl group having 1 to 4 carbon atoms.

5. An electrolyte solution composition, which comprises an electrolyte dissolved in an organic solvent (s2) comprising said compound (a2) according to claim 4.

6. An electrolyte solution composition according to claim 5, wherein said organic solvent (s2) comprises (a2) and a co-solvent (a3) selected from the group consisting of cyclic or chain carbonates, chain carboxylic acid esters, cyclic or chain ethers, lactone compounds, nitrile compounds and amide compounds, in a weight ratio of a3/a2=(0.1 to 2)/1.

* * * * *